United States Patent
Muroi et al.

Patent Number: 5,463,156
Date of Patent: Oct. 31, 1995

[54] METHOD AND APPARATUS FOR DEHYDROGENATION

[75] Inventors: Takashiro Muroi, Ushiku; Toshio Sato, Kashima; Ikuo Ito, Kashima; Kyoichi Takeda, Kashima, all of Japan

[73] Assignee: Sumikin Chemical Co., Ltd., Japan

[21] Appl. No.: 75,954

[22] Filed: Jun. 11, 1993

[30] Foreign Application Priority Data

Jun. 11, 1992 [JP] Japan .................. 4-179484

[51] Int. Cl.⁶ .................. C07C 5/32
[52] U.S. Cl. .................. 585/400; 585/410
[58] Field of Search .................. 585/400, 410

[56] References Cited

U.S. PATENT DOCUMENTS 3,781,375  12/1973  Shima et al. .................. 585/400
4,291,181  9/1981  Kiikka et al. .................. 585/400

Primary Examiner—Asok Pal
Attorney, Agent, or Firm—Harris Beach & Wilcox

[57] ABSTRACT

There is disclosed a method and apparatus for removing inhibiting substances produced in a dehydrogenation aromatization of poly cyclic compounds, the removal and consequent refinement of the reaction products occurring within the reaction system itself. To a dehydrogenation reaction apparatus comprising an evaporation section, a distillation, section, a reaction chamber including a catalyst bed section and a reflux condenser section, raw material is fed and then evaporated. After the vapor is passed through the catalyst zone section, it is liquefied at the reflux condenser section, and a portion or whole returned to the reaction chamber. The method is effective with poly cyclic compounds that cannot easily be handled by conventional methods. The reaction is highly efficient and proceeds with minimal catalyst deterioration.

10 Claims, 3 Drawing Sheets

METHOD AND APPARATUS FOR DEHYDROGENATION

BACKGROUND OF THE INVENTION

1. Field of the Invention

This invention relates to a new method and apparatus for catalytic dehydrogenation. More particularly the invention relates to a process suitable for the dehydrogenation and aromatization of alkylcyclohexane or a polycyclic compound in which a reaction inhibitor develops during dehydrogenation.

2. Description of the Prior Art

In the prior art, various methods of catalytic dehydrogenation have been employed in the chemical industry. For instance, a liquid-phase dehydrogenation reaction utilizing a fixed bed or suspensoid bed is known; and the fixed bed process has been adapted for gaseous-phase dehydrogenation, and has been widely utilized.

Chemical or mechanical methods are generally used to remove the inhibitor of the dehydrogenation reaction, particularly when dehydrogenation is accomplished by a catalytic reaction, and when the substances responsible for the inhibition are present in the starting material.

To deal with the formation of an inhibiting substance (including the reaction product of the dehydrogenation) during the dehydrogenation reaction process, it is known to conduct an operation that alters the catalyst controlling method or to become severely the reaction conditions.

In the prior art methods the inhibitor of the dehydrogenation reaction and the dehydrogenation reaction product are removed in separate processes. However, none of the state-of-the-art methods and devices is capable of removing the inhibitor from the starting materials being reacted inside the dehydrogenation reaction chamber, nor of efficiently the removing the inhibitor and of refining and separating the reaction product within the dehydrogenation reaction system.

OBJECTS AND SUMMARY OF THE INVENTION

Accordingly, it is an object of the present invention to provide an improved method and apparatus for removing an inhibitor of the dehydrogenation reaction which is present in the starting reaction material.

It is another object of the present invention to provide an improved method and apparatus for removing from the reaction system an inhibitor of the dehydrogenation reaction that is formed during the dehydrogenation reaction process.

It is yet another object of the present invention to provide an improved method and apparatus for refining and separating the reaction product from the inhibitor.

As a result of continuous and diligent research and experiments, the present inventors have discovered a method involving the combination of distillation with dehydrogenation processes, any inhibiting substances present in raw material to be dehydrogenated, and any polymerized substances produced during the dehydrogenation reaction can be separated, thereby protecting the reaction catalysts, and at the same time selectively separate the reaction products, intermediates and byproducts of the reaction. The subsequent refining of the reaction products is thereby simplified.

Namely, according to the present invention, a raw material is supplied to and evaporated in a dehydrogenation reaction apparatus comprising an evaporation section, a catalyst bed section, and a reflux condenser section. After evaporated vapor is passed through the catalyst zone, it is cooled and liquified in the reflux condenser section, and then all or part of the liquid is returned to the catalyst zone to complete the dehydrogenation process.

The present invention also provides an apparatus for performing dehydrogenation comprising an evaporation section, a catalyst bed section, and reflux condenser section.

An evaporation section, according to the present invention, is designed to evaporate raw material to be dehydrogenated, or a reaction product by the dehydrogenation, or the like. Heat, such as sensible heat from the fed raw material or heat generated by insertion of another substance can serve as an energy source for the evaporation section, and can be transferred through internal or external heat exchangers or the like.

Although vapor generated by the evaporation can be introduced to an upper, center, or lower portion of the catalyst zone, it is normally fed from the lower portion of the catalyst zone. Distillation plates are setted in the evaporation section, reflux condenser section, and the central, upper or lower portion of the catalyst bed section. Although the catalyst zone itself functions as an effective distillation plate, raw material, reaction product, intermediate products, byproducts, or inhibitors of the dehydrogenation reaction can be condensed, refined and removed more efficiently by providing additional distillation plates.

If the catalyst is a type providing a passage for vapor and liquid with better efficiency, the shape of the catalyst to be packed in the catalyst zone is not limited, but the catalyst preferably has a relatively high activity to assure efficient dehydrogenation.

Moreover, in order to better disperse the liquid, distributor can be installed.

The recycling cooling reaction is designed to cool and liquify a raw material from the catalyst zone, products, intermediate products or byproducts of the dehydrogenation reaction, or vapor having a low boiling temperature. The reflux condenser section can be either an internal top-condenser, or an external type in which the vapor is externally exhausted for cooling and the liquified vapor is recyled by a pump.

The raw material for the dehydrogenation reaction is supplied to a reaction apparatus either in a liquid-state, gaseous-state, or superheated state. The effective content of the raw material to be fed to the dehydrogenation reaction apparatus is not critical to the extent that it does not affect the function of the dehydrogenation reaction system.

If necessary, an additional component such as a hydrogen acceptor can be mixed in. The raw material for the dehydrogenation reaction can be supplied to the reactor by a batch method, a continuous method, or a semi-batch method.

The reactor is maintained at either reduced pressure, atmospheric pressure, or excess pressure in order to achieve a predetermined reaction temperature.

The fed raw material, products or byproducts by the dehydrogenation reaction are distributed inside the reaction apparatus according to their respective vapor pressures. It is apparent that the distribution will vary according to compositions and hold up amounts in each portion of the reaction apparatus. For example, if the vapor pressure of the dehydrogenation reaction product is higher than that of the raw material, it will be condensed at the upper portion of the apparatus; while if it is lower than the vapor pressure of the raw material, it will be condensed at the lower portion thereof. Namely, the raw material or dehydrogenation reaction products or byproducts can be arbitrarily distributed by installing the distillation plates, changing the recycling cooling ratio, altering pressure or manipulating the supplied and extracted amounts. Impurity in the raw material, unreacted raw material, and products or byproducts of the dehydrogenation reaction can be extracted in either vapor or liquid phase, according to requirements, from the reflux condenser section, upper, center or lower portion of the catalyst zone secton, or from the evaporation section.

Hydrogen generated by the dehydrogenation reaction is generally extracted externally fom the reflux condenser section. At this stage, any component in raw material having relatively low boiling temperature, water or low boiling component produced by the dehydrogenation reaction can be extracted as vapor.

The component liquified at the recycling cooling section, after a portion of it is extracted if necessary, is returned to the distillation plate, catalyst zone section, or the evaporation section installed inside the catalyst section.

Since the dehydrogenation reaction and separation with distillation can be achieved simultaneously at this dehydrogenation system section; the present invention possesses the following advantages;

(1) A desired concentration of the raw material can be supplied to the catalytic reaction because impurities in the raw material can be separated by distillation. Moreover, since catalyst inhibitors can be separated and removed by distillation, an additional refining process is not required.

(2) The low boiling components produced in the dehydrogenation process can be condensed at the reflux condenser section or the upper portion of the reaction apparatus; and polymerized substances, such as reaction inhibitors having high boiling points, can be concentrated at the evaporation section or the lower portion of the reaction apparatus, so that the catalyst bed section can be protected.

(3) Products, intermediates and byproducts produced by the dehydrogenation reaction can be extracted selectively, so that post-treatment processes such as a refining procedure can be eliminated.

(4) Since the raw material can be separated by distillation from the dehydrogenation reaction products, the dehydrogenation can be constantly performed at a high concentration of the raw material, resulting in an improved and favorable reaction rate. Moreover, if the dehydrogenation reaction product itself acts as a reaction inhibitor, its removal promotes still greater efficiency.

(5) Since the surface of catalyst is always washed by fresh liquid, adsorption of reaction inhibitors is minimized.

(6) Because the hydrogen vapor pressure can be markedly reduced by virtue of the vapor of the raw material or the dehydrogenation reaction products, the dehydrogenation reaction can be advantageously maintained in equilibrium. In conventional methods, reduction of the hydrogen vapor pressure can be achieved by reduced system pressure, dilution by nitrogen or steam, or by adding hydrogen acceptors including oxygen (or air) or nitro-compounds. However, in cases when reducing pressure in the reaction system is impossible due to limitations in reaction temperature, the present invention possesses a great advantage over the conventional methods.

(7) It is difficult to maintain a desired reaction temperature, particularly in the fixed bed method, since the dehydrogenation reaction is endothermic. However, according to the present invention, reaction heat is supplied by the vapor, and the catalyst temperature can be determined by the vapor temperature. Acordingly, a more stable and uniform reaction temperature can be maintained state than the in conventional methods. Furthermore, control of the reaction temperature can be achieved more easily by controlling the pressure in the reaction apparatus or the apor composition; hence it is superior to the conventional methods.

The evaporation section, catalyst bed section and the reflux condenser section can be formed as one single unit, or any two of these can be combined into a functional unit without reducing the effectiveness of the present invention. Namely, the system, according to the present invention, can be designed in such a way that the evaporation section, catalyst bed section, or the reflux condenser section can be provided externally. The distillation plates can be added if required.

As described above, the present invention is advantageously applied to substances which are difficult to dehydrogenate by conventional methods. Moreover, the present invention is more effective under relatively mild processing conditions for substances which are easily affected by reaction product inhibition such as cyclohexane, cyclooctane or alkyl derivatives. Furthermore, the dehydrogenation-aromatization of poly-cyclic compounds is relatively difficult to achieve and the catalyst easily deteriorates. Hence, the present invention is particularly effective in the case of 1,2,3,4 -tetrahydronaphthalene (hereinafter 1,2,3,4-THN) derivatives. The high degree of effectiveness, which was unexpected, was recognized with 1,4,5,8-tetraalkyl-1,2,3,4-tetrahydronaphthalene (hereinafter 1,4,5,8-TAN) which was the most difficult to dehydrogenate by steric strain.

BRIEF DESCRIPTION OF THE DRAWINGS

Further objects of the present invention, together with additional features and advantages accruing therefrom will be apparent from the following description and drawings in which.

DETAILED DESCRIPTION OF THE PREFERRED EMBODIMENT

While the present invention will be described in great details below according to embodiments, the present invention is not limited by the following embodiments.

Embodiment 1

Figure 1:
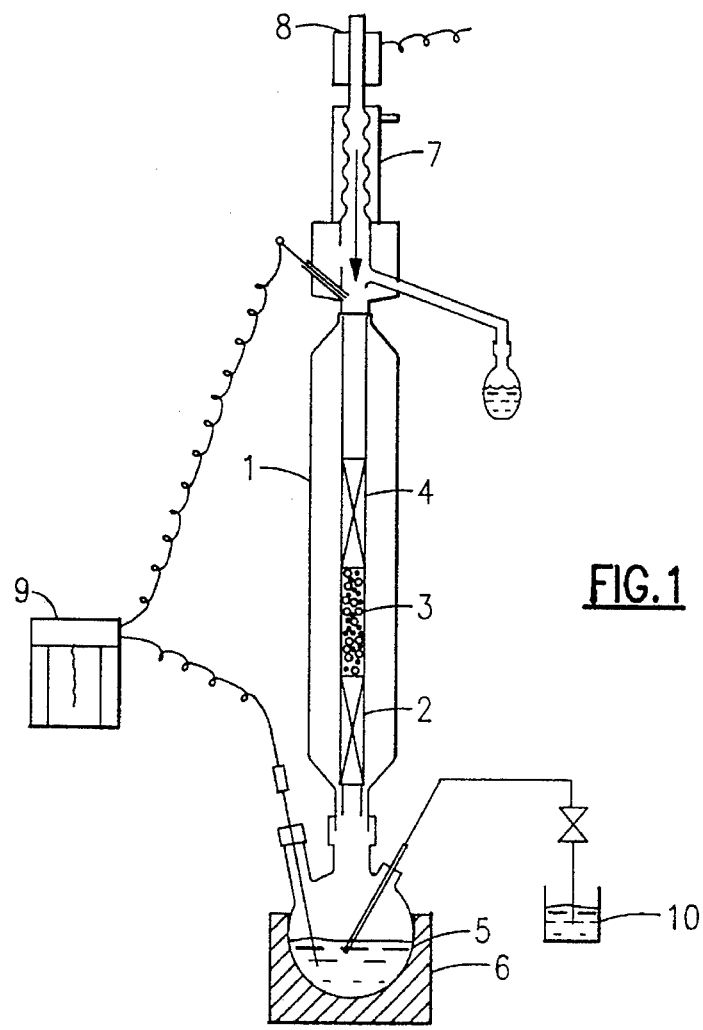
FIG. 1 is a schematic diagram of a fixed bed type dehydrogenation apparatus according to embodiments 1 and 2.

FIG. 1 is a schematic diagram of the fixed bed type dehydrogenation reaction apparatus which was employed for the dehydrogenation reaction according to the present invention.

In FIG. 1 a vacuum adiabatic column 1, 15 mm in diameter and 1 m in length, was fixed in turn with packing 2 for the distillation plates (the packing being 20 cm in height, corresponding to 10 theoretical plates) at the extreme bottom portion, dehydrogenation catalyst zone 3 (13 cm in height comprising 10 g carbon pellets containing 3% Pt with 3 mm in diameter and 3~6 mm in length thereon, and 10 cm of packing 4 for distillation plates being 10 cm in height (corresponding to 5 theoretical plates) as a top layer. In to a 200 ml three necked flask 5 which was connected to the lower portion of the vacuum adiabatic column 1, the 1,4,5,8 -tetramethyl-1,2,3,4-tetrahydronaphthalene (hereinafter 1,4, 5,8-TMT) 50 g as a raw material was placed, then heated and evaporated by a mantle heater 6, and then cooled and recycled by a condenser 7, which is connected to the upper portion of the vacuum adiabatic column 1. The recycled amount thereby obtained was 165 g/hr. It was also observed that the temperature of the catalyst zone 3 was 270° C., the catalyst zone having been heated to the boiling temperature of the raw material. When temperature of the catalyst zone 3 decreased due to the presence of low boiling substances, the electromagnetic valve 8 was selectively operated to extract a small amount of the low boiling substance. The temperatures of the upper portion and lower portion were monitored and recorded by the temperature recorder 9. The reaction process was also monitoring the raising temperature of the lower portion. Dehydrogenation product shown at 10 in FIG. 1 was also obtained.

The dehydrogenation reaction product 10 was sampled from the three necked flask 5 every one hour after the reaction started, and the concentration of the dehydrogenation reaction product was analyzed; it was found to be 1,4,5,8 -tetramethylnaphthalene (hereinafter TMN) plus 5,6-dimethylacenaphthene. The result of the analysis is presented as A in FIG. 2.

Figure 2:
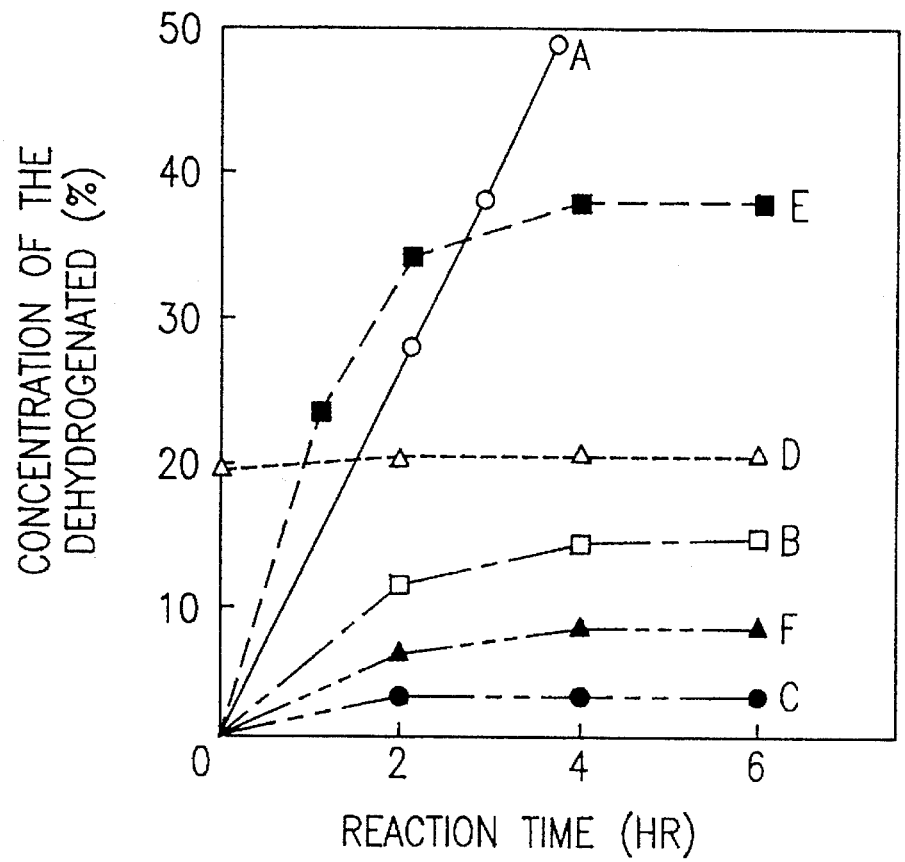
FIG. 2 graphically indicates a relationship between the reaction time and concentration of the dehydrogenation reaction, according to embodiment 1 of the invention and comparisons 1 to 3.

As seen at line A in FIG. 2, the concentration of the dehydrogenation reaction product sampled from the three necked flask 5 reached 48% after the reaction for 4 hours.

In the next step, after all reaction product was recovered from the three necked flask 5, the new raw material of 1,4,5,8-TMT 50 g was fed. After a similar reaction was repeated eight times, it was found that the concentration of the dehydrogenation reaction products was 45–50% even after the reaction for 6 hours, indicating that the catalyst had not deteriorated.

Comparison 1

Figure 3:
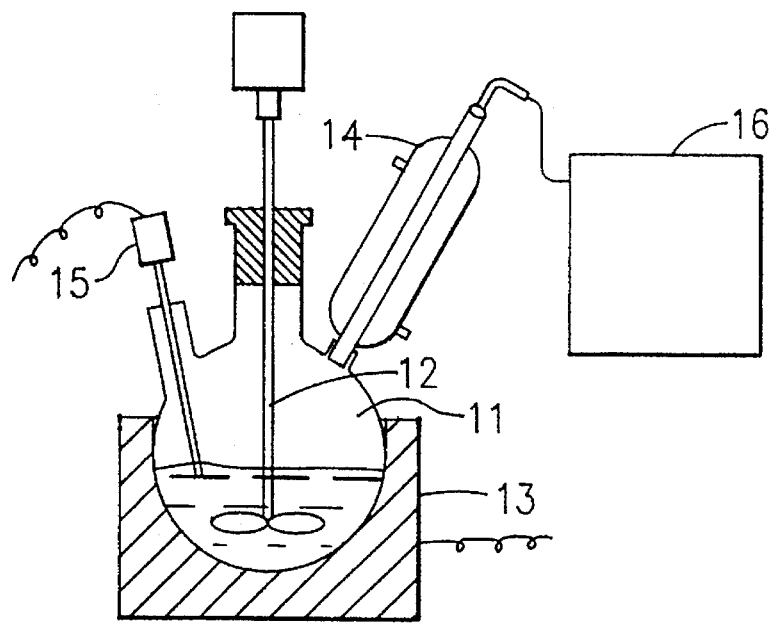
FIG. 3 is a schematic diagram of a suspension bed type of dehydrogenation reaction apparatus in accordance with comparisons 1 to 4.

FIG. 3 shows a schematic diagram of a suspensoid bed type dehydrogenation reaction apparatus, which was employed in the conventional dehydrogenation reaction.

To a 200 ml three necked flask 11 for the dehydrogenation reaction apparatus, 50 g of 1,4,5,8-TMT as raw material and 10 g of dehydrogenation catalyst of carbon pellet containing of 3% Pt having 3 mm in diameter and 3~6 mm in height 3% Pt (which was exactly the same as those used for embodiment 1) were red. They were heated and boiled by the mantle heater 13 while stirring with the stirrer 12, to continue the reaction for 6 hours by cooling and recycling through the Liebig condenser 14. The temperature raises during the reaction procedures was monitored and recorded by the thermometer (thermocouple) 15. The amount of hydrogen measured through the rubber balloon 16 was found to be of almost the theoretically predicted value.

The dehydrogenation reaction product was sampled from the three necked flask hourly after the reaction started and the concentration (of 1,4,5,8-TMN+5,6-dimethylacenaphthene) was analyzed. The result is shown in line B of FIG. 2.

As seen in FIG. 2 at line B, the reaction was remarkably slow and it did not proceed later 4 hours. It was difficult to obtain a concentration of dehydrogenation reaction products that was more than 16%.

The reaction liquid was extracted from the three necked flask 11, the catalyst was separated by the filtering at 150° C. The filtered catalyst along with new 1,4,5,8-TMT 50 g were fed to the three necked flask 11 to react for another 6 hours under the same conditions, the reaction proceeding as before. Similarly, the dehydrogenation reaction products were sampled hourly from the three necked flask 11 after the reaction had started, and the concentration of the dehydrogenation reaction product (1,4,5,8-TMN+5,6-dimethylacenaphthene) was analyzed. The result is presented in line C of FIG. 2.

As seen in line C of FIG. 2, even after another reaction for 6 hours, the concentration of the dehydrogenation reaction product was only 4.1%, indicating that the reaction did not proceed, and the catalyst had markedly deteriorated.

Comparison 2

To a 200 ml three necked flask 11 of the dehydrogenation reaction apparatus, as seen in FIG. 3, 40 g of 1,4,5,8-TMT as raw material and 10 g of refined dehydrogenation reaction products produced through embodiment 1 (namely, 1,4,5,8-TMN 36.4% and 5,6-dimethylacenaphthene 61.2%) were added to establish the initial concentration for the dehydrogenation reaction at 20%. In addition, 10 g of dehydrogenation catalyst comprising carbon pellet containing 3% Pt measuring 3 mm in diameter and 3~6 mm in length was fed. They were heated by the mantle heater 13 while stirring with the stirrer 12, and evaporated to continue the reaction for 6 hours while cooling and recycling by the Liebig condenser 14.

The dehydrogenation reaction product was sampled hourly from the three necked 11 after the reaction had started and the concentration of the dehyrogenation reaction product was analyzed. The result is shown in line D of FIG. 2.

As seen in line D of FIG. 2, the reaction barely proceeded, and the concentration of the dehydrogenation reaction product was 22.1% after 6 hours. It is suggested that the dehydrogenation reaction product per se or the contained impurity prevented the proper reaction.

Comparison 3

To a 200 ml three necked flask 11 of the dehydrogenation reaction apparatus as seen in FIG. 3, 1,4,5,8-TMT 50 g and dehydrogenation catalyst 10 g comprising powdered active carbon supported with 3% Pt were fed, heated and boiled by the mantle heater 13 while stirring with the stirrer 12. The reaction was carried out for 6 hours by cooling and recycling by the Liebig condenser 14.

The dehydrogenation reaction product was sampled from the three necked flask 11 hourly after the reaction had started, the dehydrogenation reaction products (1,4,5,8-TMN+5,6-dimethylacenaphthene) were analyzed. The result is shown in line E of FIG. 2.

As seen in line E of FIG. 2, although the reaction started very rapidly, after about 2 hours had elapsed, it no longer proceeded, and the concentration of the dehydrogenation reaction product did not exceed 38%.

In the next step, similar to comparison 1, the catalyst were recovered. The recovered catalyst was reacted with new raw material, 50 g of 1,4,5,8-TMT. As seen in line F of FIG. 2, it was found that the concentration of the dehydrogenation reaction product reached only 8.2% and the catalyst had remarkably deteriorated.

Embodiment 2

A vacuum adiabatic column 1, 15 mm in diameter and 1 m in length, was fixed in turn with packing 2 for the distillation plates (the packing being 20 cm in height, corresponding to 10 theoretical plates) at the extreme bottom portion, dehydrogenation catalyst zone 3 (13 cm in height comprising 10 g carbon pellets containing 3% Pt with 3 mm in diameter and 3~6 mm in length thereon, and packing 4 for distillation plates being 10 cm in height (corresponding to 5 theoretical plates)as a top layer. To a 200 ml three necked flask 5, which was connected to the lower portion of the vacuum adiabatic column 1, the 1,4-dimethyltetralene 50 g as a raw material was fed, then heated and boiled by a mantel heater 6, and cooled and reycled by a condenser 7, which is connected to the upper portion of the vacuum adiabatic column 1.

The dehydrogenation reaction product was sampled from the three necked flask 5 hourly after the reaction has started. The concentration of the dehydrogenation reaction product was analyzed. The result is presented in line G of FIG. 4.

Figure 4:
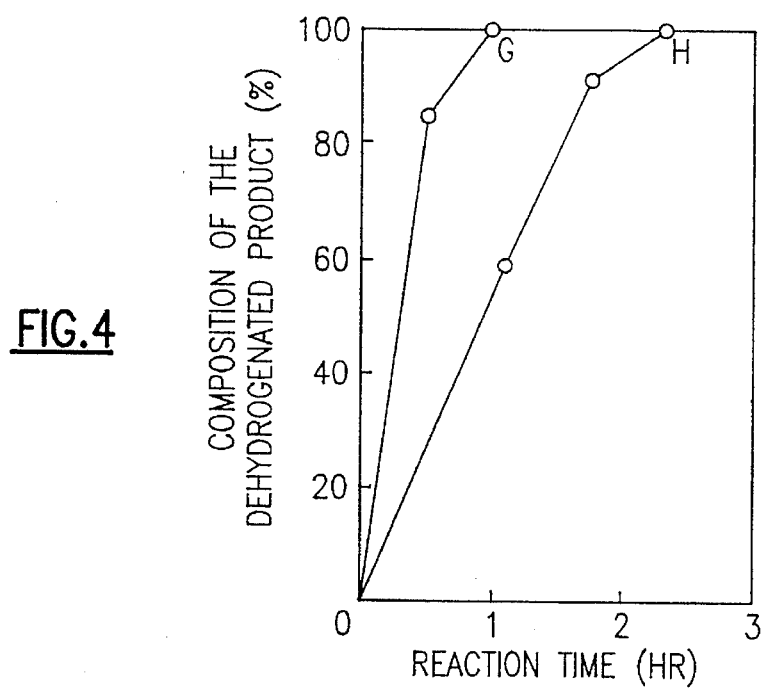
FIG. 4 graphically indicates a relationship between the reaction time and concentration of dehydrogenation reaction product in accordance with an alternate embodiment of the invention.

As seen in line G of FIG. 4, almost 100% of the fed raw material was converted to 1,4-dimethylnapthalene for one hour after the reaction had started.

Comparison 4

To a 200 ml three necked flask 11 for the dehydrogenation reaction apparatus, as shown in FIG. 3, 50 g of 1,4-dimethyl-1,2,3,4-tetrahydronaphthalene as raw material and 10 g of the dehydrogenation catalyst comprising carbon pellet containing 3% Pt, which was same as that used for embodiment 1, were fed, heated and evaporated by heating with the mantle heater 13 while stirring by the stirrer 12, followed by cooling and recycling via Liebig condenser 14.

The dehydrogenation reaction products were sampled from the three necked flask at one hour one hour and 40 minutes, and 2 hours and 20 minutes after the reaction had started. The sample was further analyzed. The result is shown in line H of FIG. 4.

As seen in line H of FIG. 4, after the reaction for 2 hours and 20 minutes, 100% of the 1,4-dimethyl-1,2,3,4 -tetrahydronaphthalene was successfully converted to 1,4 -dimethylnaphthalene.

Embodiment 3

Figure 5:
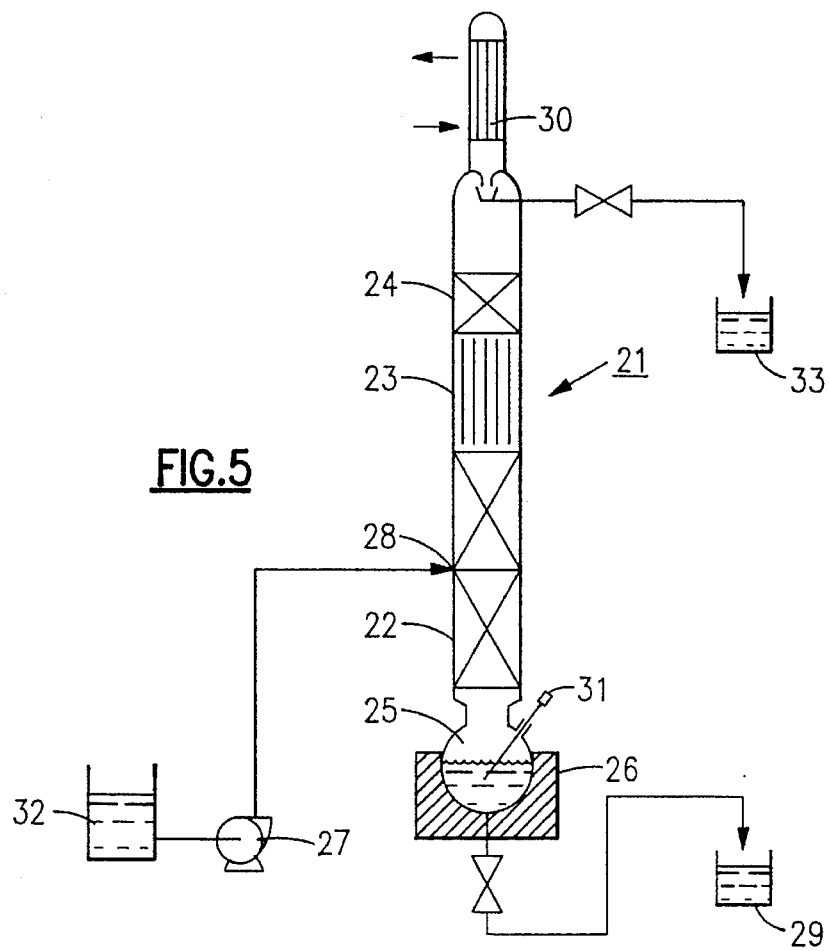
FIG. 5 is a schematic illustration of a continuous type of dehydrogenation reaction apparatus employed in another alternate embodiment 3 of the invention.

FIG. 5 shows a schematic diagram for the continuous type dehydrogenation reaction apparatus, according to the present invention.

A lower distillation column 22 (having 30 theoretical plates) was installed beneath the distillation column 21 (30 mm in diameter and 1.2 m in length), of the continuous type dehydrogenation reaction apparatus. The dehydrogenation catalyst zone 23 comprising 125 g carbon pellets containing 3% Pt measuring 3 mm in diameter and 3~6 mm in length was fixed above the lower distillation column 22. The upper distillation column 24 (having 10 theoretical plates) was further installed on top of the catalyst zone 23. The dehydrogenation reaction product (namely, 1,4,5,8-TMN and 4,6-dimethylacenaphthene) was fed to the evaporation section 25 below the column 21. The fed material was heated by the heater 26. When the temperature reached the boiling point, 312° C., the raw material of 1,4,5,8-TMT was supplied through a nozzle 28 positioned at the center portion of lower distillation plates 22 (corresponding to 15 theoretical plates) through pump 27 at a flow rate of 46.2 g/hr. The reaction product 29 was extracted with a corresponding amount of the supplied amount of the raw material from the bottom portion of the evaporation section 25, cooled and recycled to the upper portion of the column 21 which is connected to the condenser 30, to proceed a continuous reaction. In FIG. 5, there are also a thermometer 31, raw material tank 33, and the low boiling material 33.

Moreover, a small amount of low boiling material which is found in the raw material and a small amount of low boiling material from the upper portion of the column 21 was extracted as the low boiling material 33 of the dehydrogenation reaction product in order to maintain the reaction temperature of the catalyst zone 23. The amount extracted was 0.5~1.0% of the raw material.

The reflux rate at the steady state was 760 g/hr.

After a 20 hour continuous operation, the dehydrogenation reaction product 29 was sampled and analyzed. The results showed that the total fraction was 98.1%, of which 65.4% was 1,4,5,8-TMN, and 32.7% was 5,6-dimethylacenaphthene.

While the weight and composition of the reaction products were analyzed every 20 hours, the whole reaction was continued for 120 hours. The changes in concentration of the dehydrogenation reaction product during the continuous reaction is shown in FIG. 6.

Figure 6:
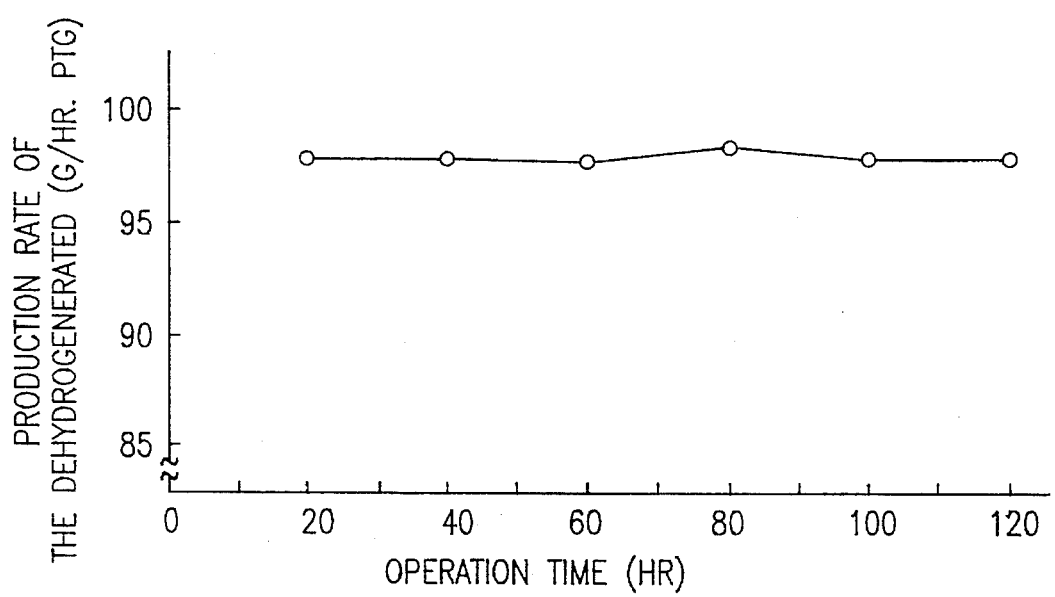
FIG. 6 is a graph that indicates a relationship between the operation time and concentration of the dehydrogenation reaction products according to the embodiment of FIG. 5.

As seen in FIG. 6, it was found that the concentration of the dehydrogenation reaction product was maintained fairly constant during the 120 hour continuous operation.

As described above, according to the present invention, the dehydrogenation of poly-cyclic compounds, which are difficult to process by conventional methods, can be effectively achieved without deterioration of the catalyst. In particular, 1,4,5,8-TMT which is the most difficult to dehydrogenate by steric strain was dehydrogenated with the highest efficiency. This result was better than the inventors anticipated.

While this invention has been explained with reference to the processes described herein, it is not confined to the details as set forth and this application is intended to cover any modifications and changes as may come within the scope of the following claims.

What is claimed is:

1. A method of dehydrogenation, comprising the steps of:
   feeding a raw material into a reaction apparatus comprising an evaporation section, a catalyst bed section, and a reflux condenser section for a vapor;
   producing a vapor in said evaporation section;
   passing said vapor through said catalyst bed section; then
   liquefying said vapor in said reflux condenser section; and returning at least a portion of a liquid obtained by liquefying said vapor to said catalyst bed section.

2. The method according to claim 1, wherein said raw material is a derivative of 1,2,3,4-tetrahydronaphthalene.

3. The method according to claim 2, wherein said 1,2,3,4-tetrahydronaphthalene derivate is 1,4,5,8-tetraalkyl-1,2,3,4-tetrahydronaphthalene.

4. The method according to claim 3, wherein said raw material is fed continuously, and further comprising the step of continuously extracting a dehydrogenation reaction product.

5. The method according to claim 1, wherein said raw material is fed continuously, and further comprising the step of continuously extracting a dehydrogenation reaction product.

6. The method according to claim 5, wherein said step of continuously extracting comprises the step of obtaining distillates from said catalyst bed section.

7. The method according to claim 6, wherein said catalyst bed section has a lower, central and an upper portion, and said step of obtaining distillates is performed in a plurality of a said portions.

8. The method according to claim 7, wherein said step of continuously extracting further comprises the steps of obtaining additional distillates from at least one of said evaporation section and said reflux condenser section.

9. The method according to claim 1, further comprising the step of maintaining said catalyst bed section at a temperature that is substantially a boiling point of the raw material while said steps of liquefying said vapor and returning a portion of said liquid to said catalyst bed section are being performed.

10. The method according to claim 9, further comprising the step of extracting catalytic inhibitors from the reaction apparatus by distillation.

* * * * *